(12) United States Patent
Noble

(10) Patent No.: US 10,843,102 B2
(45) Date of Patent: Nov. 24, 2020

(54) RESINOUS COMPOUND CRYSTALLIZATION USING NON-POLAR SOLVENT SEQUENCE

(71) Applicant: Senti Solutions Inc., Guelph (CA)

(72) Inventor: Linden Noble, Guelph (CA)

(*) Notice: Subject to any disclaimer, the term of this patent is extended or adjusted under 35 U.S.C. 154(b) by 0 days.

(21) Appl. No.: 16/456,969

(22) Filed: Jun. 28, 2019

(65) Prior Publication Data
US 2020/0001201 A1    Jan. 2, 2020

Related U.S. Application Data

(60) Provisional application No. 62/691,662, filed on Jun. 29, 2018.

(51) Int. Cl.
| | | |
|---|---|---|
| *B01D 9/00* | (2006.01) | |
| *C07D 311/80* | (2006.01) | |
| *C07C 37/84* | (2006.01) | |
| *C07C 63/66* | (2006.01) | |

(52) U.S. Cl.
CPC ......... *B01D 9/0054* (2013.01); *B01D 9/0059* (2013.01); *C07C 37/84* (2013.01); *C07C 63/66* (2013.01); *C07D 311/80* (2013.01); *B01D 2009/0086* (2013.01)

(58) Field of Classification Search
CPC .... B01D 9/0054; B01D 9/0059; C07C 37/84; C07C 63/66; C07D 311/80
USPC ........................................................ 549/390
See application file for complete search history.

(56) References Cited

U.S. PATENT DOCUMENTS

| | | | |
|---|---|---|---|
| 2,083,700 A | 6/1937 | Forrest et al. | |
| 7,900,473 B2* | 3/2011 | Takegami | B01D 9/0009 62/123 |
| 9,950,976 B1* | 4/2018 | Keller | C07C 37/004 |
| 2006/0167283 A1* | 7/2006 | Flockhart | C07C 37/70 549/390 |
| 2010/0081842 A1* | 4/2010 | Gao | B01J 31/143 564/12 |

(Continued)

FOREIGN PATENT DOCUMENTS

| | | | | |
|---|---|---|---|---|
| WO | WO-2016153347 A1 * | 9/2016 | | C07C 37/004 |
| WO | WO-2019020738 A1 * | 1/2019 | | B01D 11/04 |

OTHER PUBLICATIONS

Loewenthal, H. J. E.; "Isolating and Purifying the Product", Chapter 5 in a Guide for the Perplexed Organic Experimentalist, Second Edition, Wiley & Sons, 1990, pp. 121-153. (Year: 1990).*

(Continued)

*Primary Examiner* — Daniel R Carcanague

(57) ABSTRACT

A resin containing a desirable compound is extracted from plant material and dissolved in a volatile non-polar solvent. The solvent is evaporated, cooling the solution and increasing the saturation level of the compound in the solution. A second volatile non-polar solvent, in which the compound is less soluble, is then added to the solution and evaporated. This again cools the solution and increases the saturation level until the compound has started to crystallize. The crystals are then filtered and rinsed. Crystallization is more rapid compared to traditional techniques. The resin is obtained from the plant material using an extraction solvent to form a solution, which is then floated above an immiscible liquid, where it is drawn off through a screen and the extraction solvent evaporated.

16 Claims, 6 Drawing Sheets

(56) References Cited

U.S. PATENT DOCUMENTS

| | | | |
|---|---|---|---|
| 2017/0008870 A1* | 1/2017 | Dibble | C07D 311/80 |
| 2018/0000879 A1* | 1/2018 | Nadal Roura | A61K 36/185 |
| 2018/0162828 A1* | 6/2018 | Nadal Roura | B01D 11/0492 |
| 2018/0273501 A1* | 9/2018 | Robertson | B01D 9/0022 |
| 2018/0344785 A1* | 12/2018 | Robertson | A61K 36/185 |
| 2019/0010110 A1* | 1/2019 | Oroskar | A61K 31/05 |
| 2019/0201809 A1* | 7/2019 | Nadal Roura | G01N 30/88 |

OTHER PUBLICATIONS

Jacob; J. Chem. Soc., 1940, 649-653. DOI: 10.1039/JR9400000649 (Year: 1940).*

Mechoulam; Chem. Rev. 1976, 76, 75-112. (Year: 1976).*

\* cited by examiner

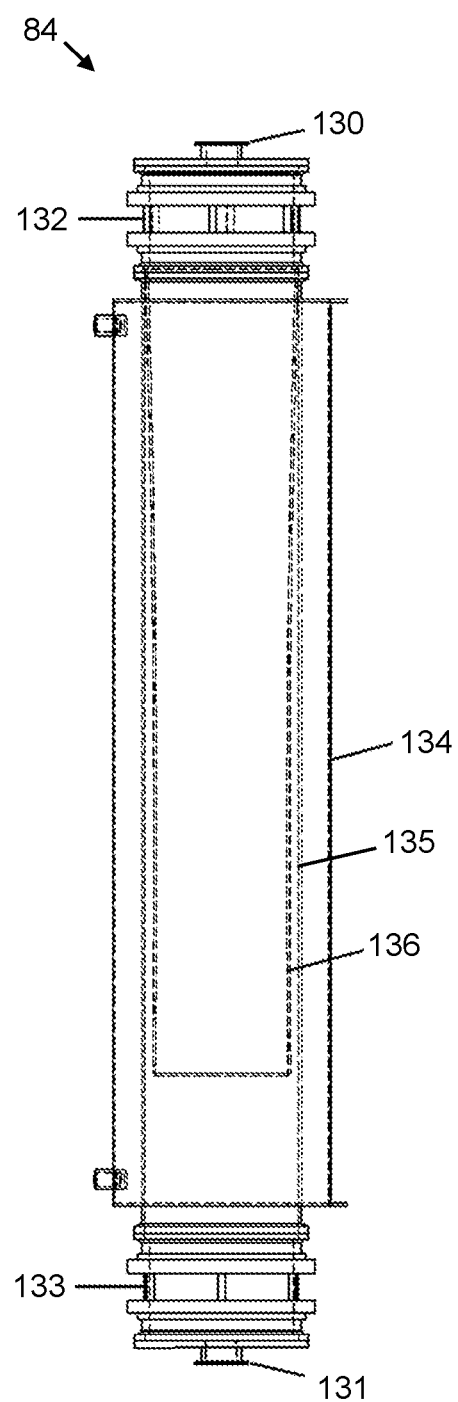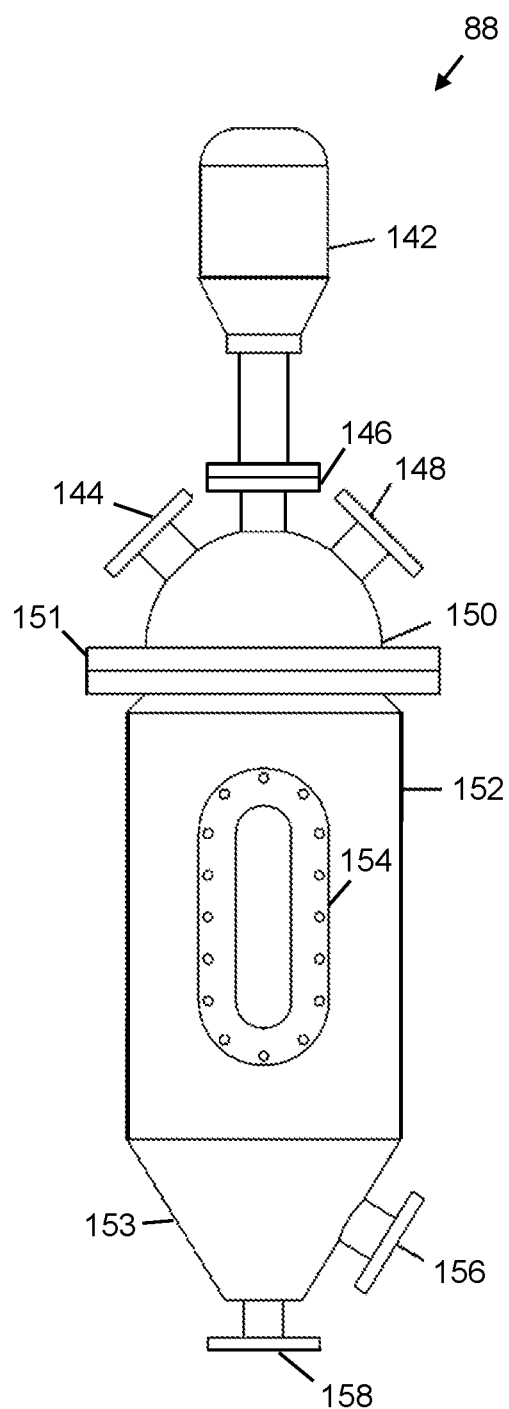
FIG. 4
FIG. 5

RESINOUS COMPOUND CRYSTALLIZATION USING NON-POLAR SOLVENT SEQUENCE

TECHNICAL FIELD

This application relates to a system and method for crystallizing desirable compounds from extracted plant resins. More specifically, it relates to a system and method that uses a sequence of volatile non-polar solvents that provide diminishing solubility, which are evaporated to cool the mixture and force crystallization.

BACKGROUND

Many extracted plant resins contain numerous desirable compounds, which can be isolated to make various high-value end products. In some cases this isolation is best performed by crystallization.

Extractions with solvents have been performed for millennia. Typically, a solvent is passed through an organic material, such as plant material, in order to dissolve and remove a desirable compound that is chemically and physically bound in the material. A resin or oil is usually obtained by the extraction, and contains the compounds that can then be crystallized. The solvent is typically a hydrocarbon, selected for its ability to dissolve the resin being extracted. Other considerations for selection of the solvent are its physical properties, boiling point, viscosity, and the solubility of undesirable compounds from the organic material in the solvent.

In many systems the method for separating the resin from the material is the same. The solvent is passed through the material where it strips out the resin, forming a solution. The solution is then filtered to mechanically remove the unwanted material solids. The solvent is then evaporated out from the solution, leaving behind only the desired resin. The desired resin is then processed to result in various products.

Crystallization of desirable cannabinoids from extracted plant resins allows for a wider range of desirable and valuable end products to be produced. Current commonly used crystallization techniques exist for crystallizing desirable cannabinoids, however they present issues related to speed and scalability.

In one technique, the extracted solution is allowed to slowly evaporate the solvent out of solution in a pressurized vessel. This increases saturation and causes large crystals to grow. This is effective, however it takes place over the course of days, weeks, or months, presenting a clear bottleneck in production.

In a second technique, the solution is actively cooled to an extremely low temperature, frequently in a cryogenic freezer. The decreased temperature causes crystallization of the desired compounds by decreasing their solubility in the solution. Again, this presents an issue, as this process generally takes weeks to complete.

Both the above techniques can be described as closed loop systems and represent systems in which the solvent is recovered for reuse in further extractions. In a third technique, normally described as an open system, the solvent is evaporated off into the atmosphere and is not recovered.

This background information is provided to reveal information believed by the applicant to be of possible relevance to the present invention. No admission is necessarily intended, nor should be construed, that any of the preceding information constitutes prior art against the present invention.

SUMMARY OF INVENTION

This system and method disclosed herein pertains to a technique for rapid crystallization of desirable compounds from an extracted plant resin containing a mixture of compounds, in particular cannabinoids. More specifically, the cannabinoids are tetrahydrocannabinolic acid (THCA), cannabidiolic acid (CBDA) and cannabidiol (CBD).

The disclosed method allows for solvent to be passed through large volumes of plant material in which a desirable compound is bound. The solvent removes a resin containing the compound, creating a solution, which is then floated to the top of a mixture with an immiscible liquid. The solution is drawn off through a screen and then filtered to remove the smaller particulates. The solution is then passed through an evaporator to recover solvent, leaving behind the extracted resin.

The resin is then transferred into a pressure vessel, where it is pressurized and treated with a series of solvents of decreasing solubility. The decrease in solubility combined with decreasing the pressure and temperature causes crystals to form in hours. The crystals are then washed in a solvent in which they are insoluble, and then the wash solvent is evaporated to leave the pure, crystallized compound, or compounds. Crystals may be produced with extremely high purity in this way.

The method of crystallization disclosed herein provides an advantage over currently used techniques in its speed, efficiency, scalability, usability and the reduction of labor. The use of solvent mixtures and pressure manipulation in a pressure vessel drastically decreases the usual production bottleneck of crystallization. Selecting solvents with appropriate boiling points reduces the need for chillers or cryogenic freezers for directly cooling the solution of resin, and promotes rapid crystallization by boiling the solvent off from within the vessel instead of cooling from the outside. The method of crystallization disclosed herein also takes weeks off latency times, and can be performed in-line, which lessens operator input and speeds up downstream processes. For example, crystallization can be achieved in hours rather than weeks. The system may be used in-line or in a batch process. In either case, generally large quantities of material may be processed. Each embodiment of the present invention provides one or more of the advantages mentioned herein.

Disclosed herein is a method for crystallizing a compound from a resin, comprising: mixing a first solvent with the resin to form a solution; evaporating the first solvent from the solution; then, mixing a second solvent with the solution, wherein the compound has a lower solubility in the second solvent than in the first solvent; removing the second solvent from the solution to cause a temperature of the solution to drop and the compound to form crystals. In some embodiments, the first solvent has a higher boiling point than the second solvent. In some embodiments, the first solvent is miscible with the second solvent.

BRIEF DESCRIPTION OF DRAWINGS

The following drawings illustrate embodiments of the invention and should not be construed as restricting the scope of the invention in any way.

FIG. 4 is a drawing representing the filtration units of the crystallization system, according to an embodiment of the present invention.

FIG. 5 is a drawing representing the crystallization vessel of the crystallization system, according to an embodiment of the present invention.

DESCRIPTION

A. Glossary

Cannabinoids are a group of chemicals that act on cannabinoid receptors in the body, numerous of which are found in the cannabis plant.

Cannabidiol (CBD) refers to a phytocannabinoid molecule that is found in only small amounts in cannabis plants and is usually obtained, after heating, from the CBDA found in cannabis plants.

Cannabidiolic acid (CBDA) is a non-psychoactive cannabinoid and the acidic precursor to CBD, and can be found in cannabis plants. CBDA converts to CBD through decarboxylation, which occurs when cannabis is exposed to heat or sunlight.

Condenser—refers to a device used for condensing a substance from its gaseous state to its liquid state.

Resin—a solid or viscous substance obtained from a plant or tree, or from a synthetic source, containing one or more organic compounds.

Solvent—a liquid in which a solid or other liquid dissolves. Multiple solvents are used herein including an extraction solvent, used for extracting resin from plants; crystallization solvents used for dissolving the resin and then forming crystals; and a wash solvent for rinsing the crystals. Note that the same solvent may be used for multiple process steps, for example, butane and propane are both used in extraction, crystallization and rinsing. However, they are generally used at different temperatures and pressures depending on the particular process.

Tetrahydrocannabinol (THC) refers to a phytocannabinoid molecule that is found in only small amounts in cannabis plants and is known for its psychoactive effect when consumed or inhaled. It is more correctly known as delta-9-tetrahydrocannabinol.

Tetrahydrocannabinolic acid (THCA) is a non-psychoactive cannabinoid found in cannabis. THCA is the acidic form and precursor to THC. THCA converts to THC via decarboxylation when exposed to heat or sunlight.

B. Overview

Figure 1:
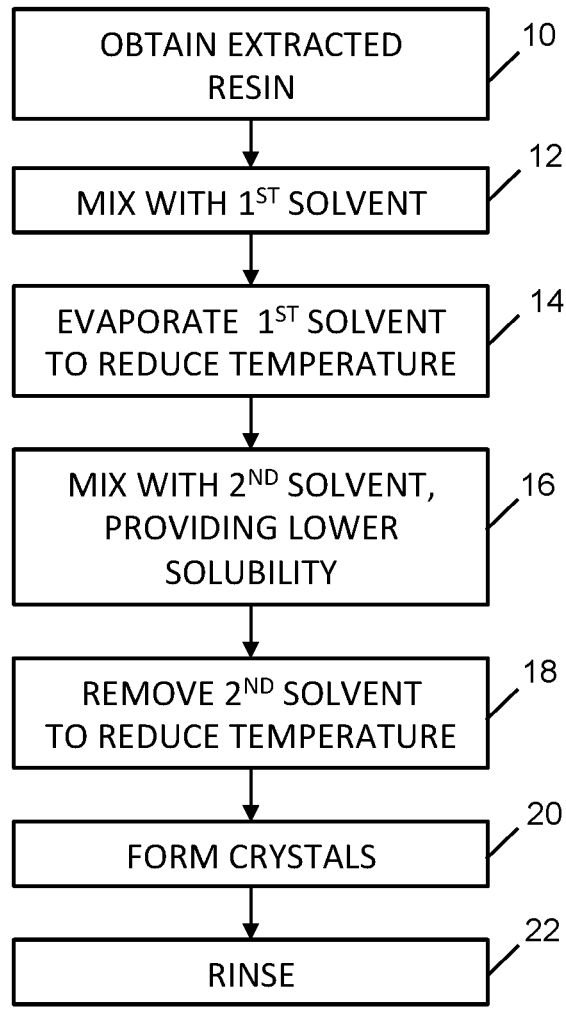
FIG. 1 is a flowchart representing the main steps of the extraction and crystallization method, according to an embodiment of the present invention.

Referring to FIG. 1, there is shown a flowchart of the main steps of the method of crystallization. In step 10, the extracted resin or oil is obtained from the plant material. The resin may or may not be decarboxylated. However, if the resin is decarboxylated, the THC will not crystallize but the CBD will. In step 12, a first solvent is added to the extracted resin and mixed to form a solution. The first solvent is then, in step 14, gradually evaporated from the solution and removed to reduce the temperature of the solution. This causes the solubility of the desired compound in the solvent to reduce and the saturation level to increase, and may at this point trigger crystal precipitation.

In step 16, a second solvent is added to the solution. The extracted compound has a lower solubility in the second solvent than in the first solvent. In step 18, the second solvent is removed, again to reduce the temperature. As a result, the overall solubility of the compound in the solvents is further reduced and crystals of the compound form, in step 20. When the crystals have been formed, they are then rinsed, in step 22.

C. Exemplary Apparatus

Figure 2:
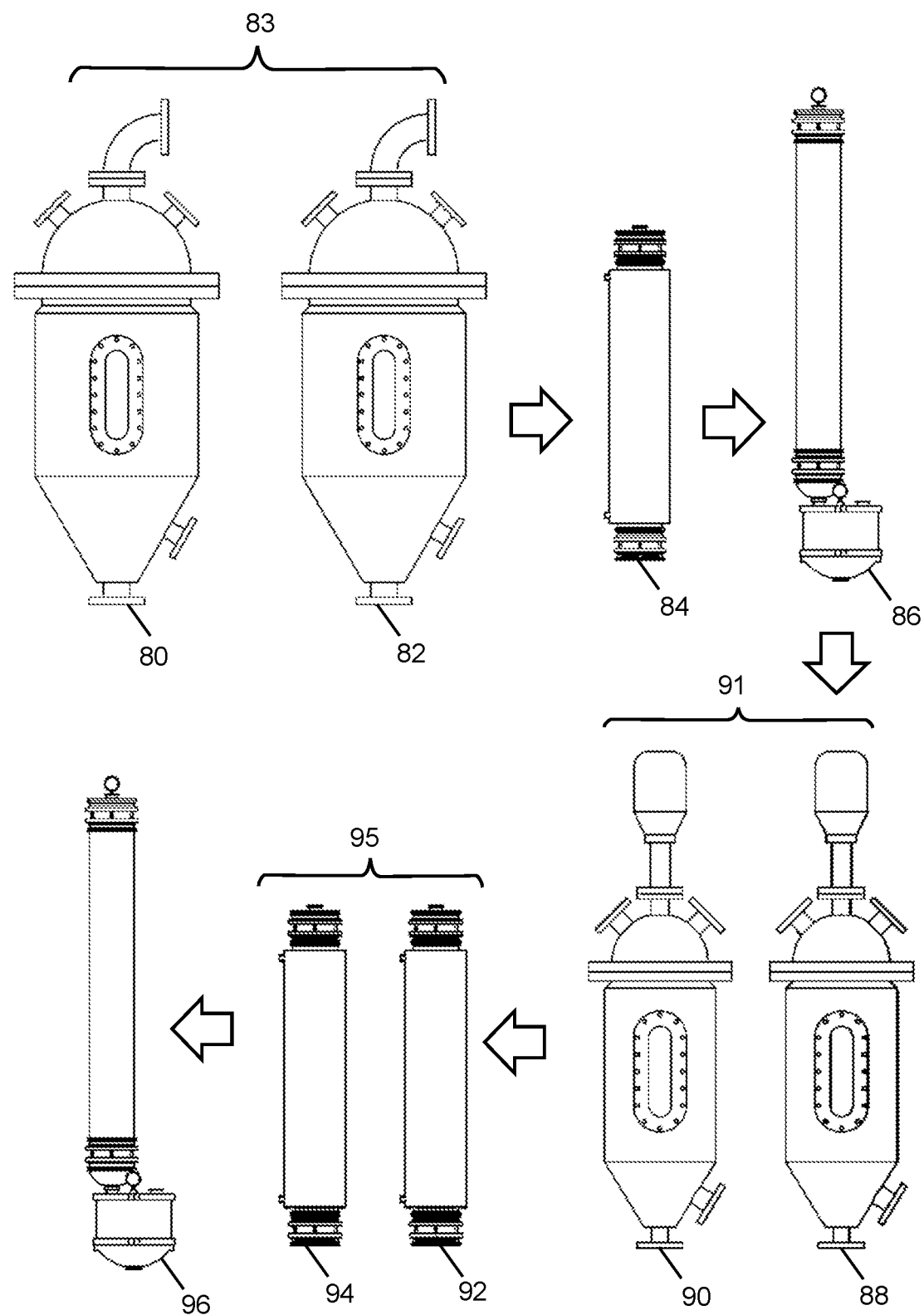
FIG. 2 is a drawing representing a crystallization system, according to one embodiment of the present invention.

Referring to FIG. 2, an example of the system as a whole is shown, with individual components being shown in more detail in subsequent FIGS. 3-6 according to function.

The extraction vessels 80, 82 forming pair of extraction vessels 83 may, for example, be stainless steel, with capacity 150 L, and pressure rated to 1.0 MPa (150 psi). The filtration unit 84, downstream of the extraction vessels 83, may typically be a stainless steel spool with a stainless steel sock filter inside. The evaporator unit 86, downstream of the filtration unit 84, may be typically stainless steel, and includes a boiler and chilled condenser for solvent recovery. The evaporator unit 86 may use a falling film for boiling to decrease degradation of the desired compound.

The crystallization vessels 88, 90 forming pair of crystallization vessels 91 are downstream of the evaporator unit 86. The crystallization vessels 88, 90 may, for example, be stainless steel of 50 L capacity and have a pressure rating of 1.0 MPa (150 psi). The crystallization vessels 88, 90 are equipped with an agitation unit for stirring the contents. Downstream of the crystallization vessels 88, 90 are the crystal washing columns 92, 94 forming a pair of crystal washing columns 95. The crystal washing columns 92, 94 are similar in construction to the filtration unit 84. The final evaporator unit 96 is similar in construction to the evaporator unit 86.

Figure 3:
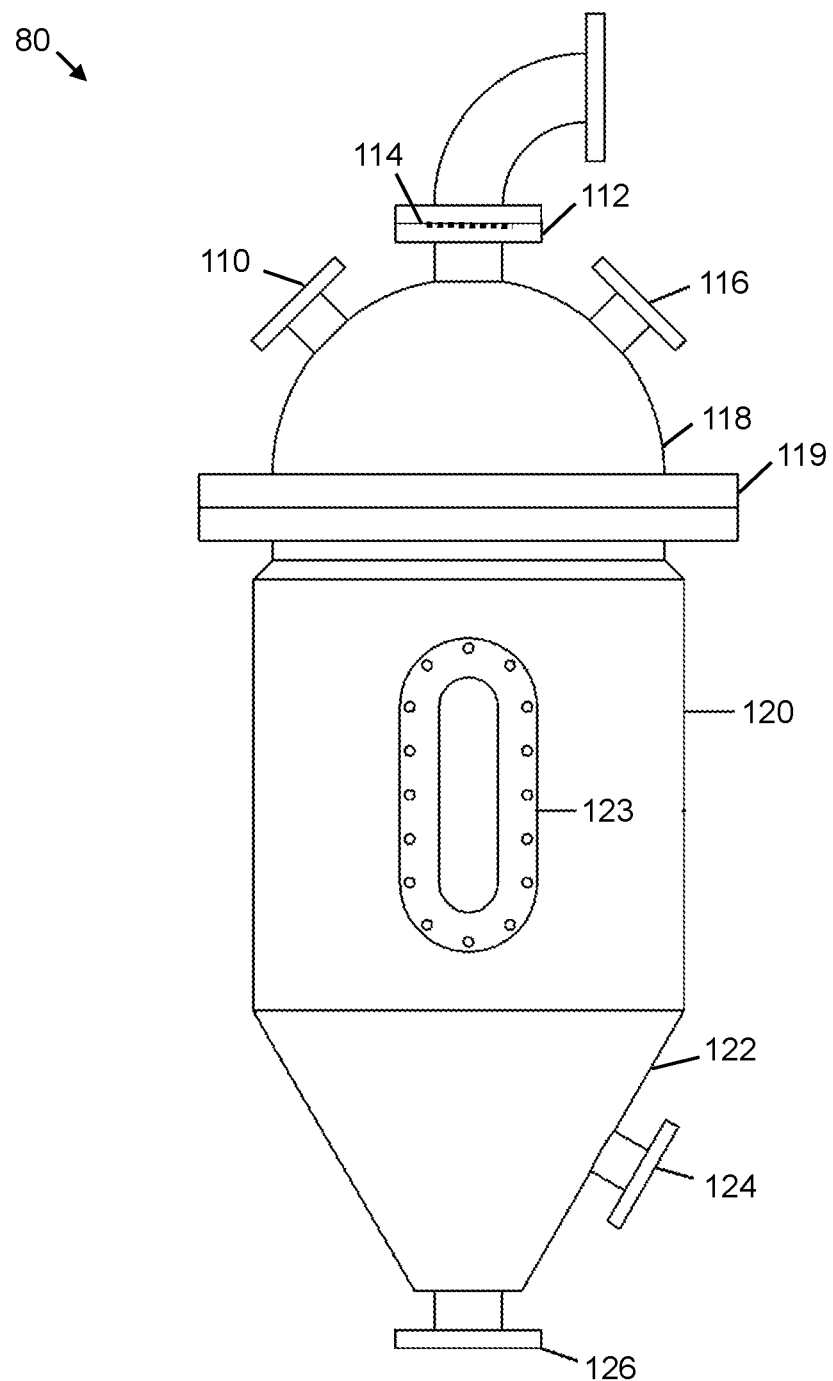
FIG. 3 is a drawing representing the extraction vessels of the crystallization system, according to an embodiment of the present invention.

FIG. 3 shows the extraction vessel 80. The elements of the extraction vessel are typically stainless steel. A large port 110 is present near the top of the extraction vessel 80 for the injection of plant material. The removal port 112 typically has a screen filter 114 extending across its cross-section. The screen filter 114 can be removed during the initial solvent flood to insert an agitator if additional mixing is required. The screen filter 114 is used to prevent solid, unwanted or spent plant material from travelling out through the removal port 112. A second large port 116 is available to install a sensor to better monitor the extraction. For example, the sensor may be a thermometer. The hemispherical tank cap 118 is typically outfitted with a 1.0 MPa (150 psi) flange 119. The extraction vessel main body 120 typically has a conical base 122 to minimize transfer loss and enhance mixing ability. Also, the conical base 122 may be outfitted with a low volume jacket for process temperature control. A large sight glass 123 allows for process viewing and monitoring. Drainage port 124 is typically fitted with an adjustable decanting tube for precise level control. The large bottom port 126 is the inlet through which the initial solvent and the immiscible liquid are added. Also, once the solution with the desired compound has been removed through the top port 112, the unwanted solid plant material and the immiscible liquid may be removed through large bottom port 126. All ports on the extraction vessel 80 are typically fitted with 1.0 MPa (150 psi) flanges and chemically compatible flange gaskets.

FIG. 4 shows the filtration unit 84, which is the same as filtration units 92, 94. The filtration unit 84 has top inlet port 130 and bottom inlet port 131. Top sight glass 132 and bottom sight glass 133 allow an operator to monitor the process occurring inside the filtration unit 84. The filtration unit 84 has a sock filter 136, which is typically stainless steel, which has a mesh size that is small enough that additional particulate material is removed. The top of the sock filter 136 may be fitted with a compatible gasket to keep it in place. The filter container 135 is typically a jacketed stainless steel spool, surrounded by jacket 134. All connections between caps, sight glasses, and spools may be held using tri-clamp connectors with compatible gaskets. Filtration of the solution through a sock filter 134 or similarly styled filter increases downstream efficiency of the process without limiting flow rate.

FIG. 5 shows the crystallization vessel 88. A high torque agitator 142 is used to effectively blend the resin with the crystallization solvents. Large ports 144, 146, 148 may be used to control pressure inside the crystallization vessel 88. A hemispherical cap 150 is typically fitted with a 1.0 MPa (150 psi) flange 151. The main tank body 152 typically has a conical base 153 to minimize transfer loss and enhance mixing ability. Also, the conical base 153 may be outfitted with a low volume jacket for process temperature control. A large sightglass 154 allows an operator to monitor processing inside the crystallization vessel 88. A drainage port 156 is typically fitted with an adjustable decanting tube for precise level control. A large bottom port 158 is present, through which solvents are injected and crystals are removed. All ports may be fitted with 1.0 MPa (150 psi) flanges and chemically compatible flange gaskets.

Figure 6:
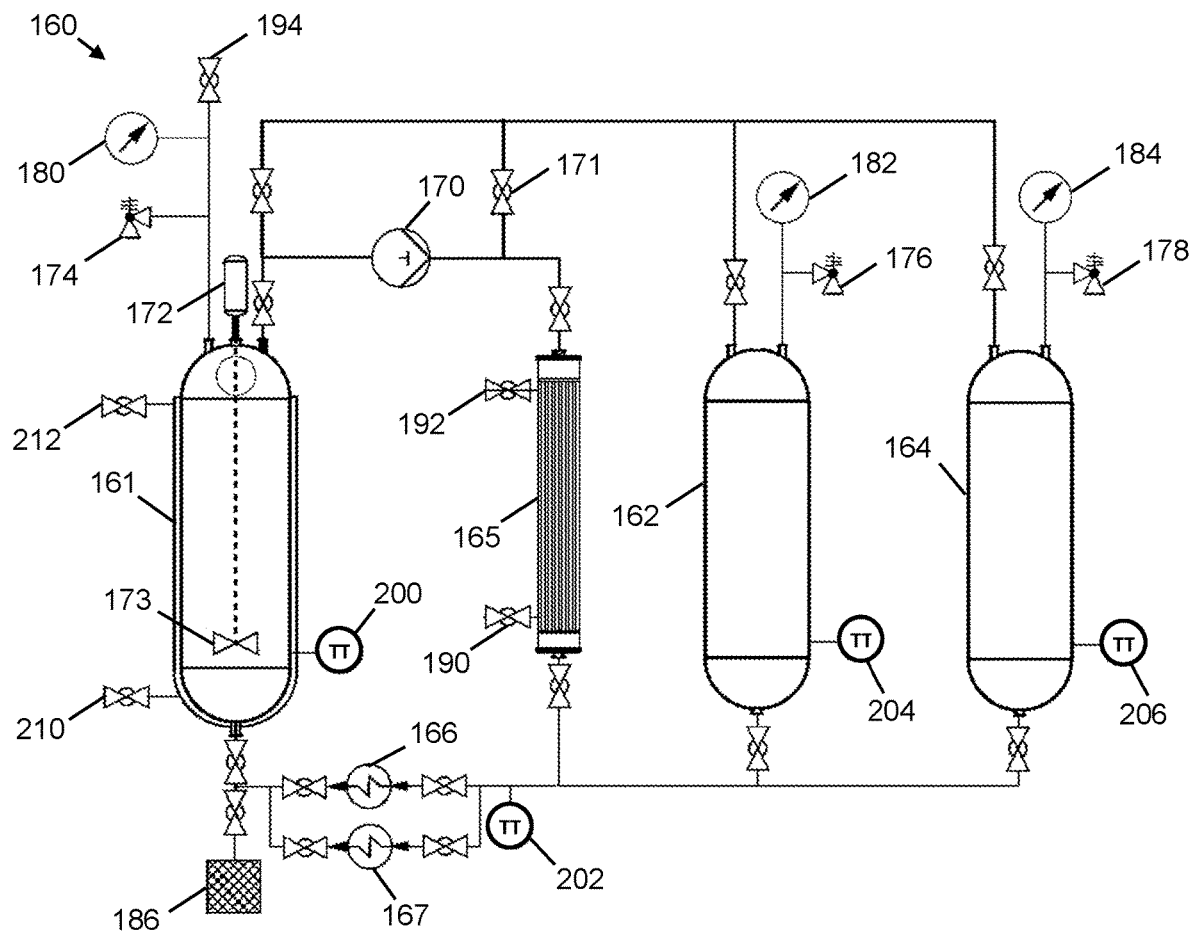
FIG. 6 is a drawing representing a crystallization system, according to another embodiment of the present invention.

FIG. 6 corresponds to elements 88 and 90 of FIGS. 2 and 5, and shows a crystallization system 160, comprising jacketed crystallization vessel 161, butane storage tank 162, propane storage tank 164, and condenser 165. The jacketed crystallization vessel 161, butane storage tank 162 and propane storage tank 164 are rated to a pressure of 2.8 MPa (400 psi).

A heat exchanger 166, for example a 15 m (50 ft), 13 mm (½") OD stainless coil in a dry ice and isopropyl bath, is used for cooling the butane or propane before it enters the bottom of the crystallization vessel 161. Heat exchanger 167 is used for the heating the butane or propane to increase the solubility it provides as it enters the crystallization vessel 161.

The condenser 165 a shell and tube condenser, which is cooled to −40° C. with a cold circulation fluid. The condenser 165 is used to condense butane and propane gas removed from the crystallization vessel 161 and is also used for manipulation of pressure inside the crystallization vessel.

A gas pump 170, for example an air operated positive displacement gas pump capable of pulling 97 kPa (14 psi) vacuum at its inlet and pressurizing its outlet to 1.4 MPa (200 psi), is connected between the crystallization vessel 161 and the condenser 165. Gas bypass valve 171 is included for the purpose of using the pump 170 to create a pressure head in the butane storage tank 162 or propane storage tank 164. Creation of the pressure head is useful for emptying the butane and propane storage tanks 162, 164.

An air-operated, high torque motor 172 is used for driving an agitator 173 inside the crystallization vessel 161. The agitator 173 may be a high shear agitator blade, coupled to the air-operated high torque motor 172 via a 25 mm (1") shaft. The high-torque motor 172 is mechanically sealed for pressure up to 2.8 MPa (400 psi) and full vacuum operation.

Pressure relief valves 174, 176, 178, which are set to 1.7 MPa (250 psi), are present on the jacketed crystallization vessel 161, butane storage tank 162, propane storage tank 164 respectively, and are vented to a safe location, typically to atmosphere through a flare stack. Pressure gauges 180, 182, 184 on the jacketed crystallization vessel 161, butane storage tank 162 and propane storage tank 164 have suitable ranges for their operation, for example from vacuum to 2.1 MPa (300 psi).

Filter 186 prevents crystals from leaving the crystallization vessel 161 during the rinsing process. The filter 186 may be, for example, a 20 µm pore size flat plate filter or a sock filter.

The condenser 165 has a cold fluid inlet 190 and a cold fluid outlet 192, which are used to create a cold fluid circulation loop that removes the heat of condensation from the condenser 165. The cold fluid is any fluid that remains fluid down to −60° C., for example, with good thermal transfer properties. In practice a Dynalene™ fluid is used. This fluid is chilled by a chiller (not shown), or a coil in dry ice and ethanol.

Inlet 194 to the crystallization vessel 161 allows resin to be injected into the crystallization system 160. The system 160 includes temperature transmitters 200, 202, 204, 206 for process monitoring. Heat transfer fluid inlet 210 and outlet 212 used for heating and cooling the crystallization vessel.

B. Exemplary Method

Figure 7:
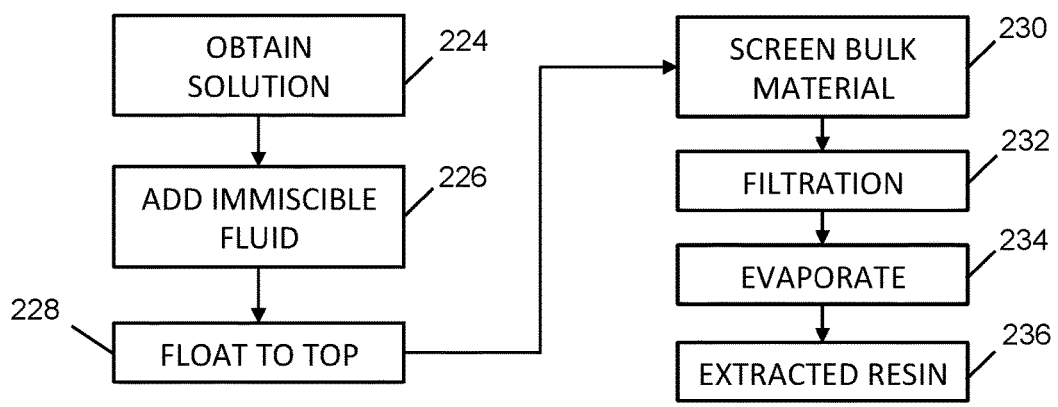
FIG. 7 is a flowchart representing a method to obtain an extracted resin from a solution, according to an embodiment of the present invention.

Referring to FIG. 7, a preliminary method is shown for first obtaining the resin, which is used as the starting substance in FIG. 1. It is a flotation separation technique with screening, which ensures that all undesirable particulates are removed from the solution before it reaches downstream processing. i.e. crystallization.

An extraction vessel is filled with the plant material to be subjected to extraction, and air in the vessel is evacuated with a vacuum pump. Liquid solvent, such as butane, propane, pentane, hexane, heptane or octane, is pumped from a solvent tank into the extraction vessel, which is filled such that a 1:1 weight to volume ratio is achieved, i.e. 1 kg of material to 1 liter of solvent. In some embodiments the ratio can be between this and 1 kg of material to 3 liters of solvent. The mixture of solvent and plant material are agitated and/or left to soak until an adequately saturated solution is formed, in step 224.

In step 226, the bottom of the extraction vessel holding the solution and plant matter is flooded with a liquid that is immiscible with the solvent. This immiscible liquid is typically water. As the immiscible liquid is denser than the solution, it causes the solution to float up to a removal port at the top of the extraction vessel in step 228.

In step 230, the bulk of the plant material that is mixed with the solution is then separated from the solution as the solution flows through a screen inline with the removal port. Recovering the solution of the solvent and resin using an immiscible liquid allows for the easy separation of the desired compound from the plant material, with minimal use of mechanical separation techniques and low energy usage.

The solution is pumped from the removal port into a filtration unit in which small particulates are filtered out, in step 232. In the filtration unit, the filtration may be assisted through the use of a vacuum pump downstream of the filter. The filtered solution is then pumped into a preheated evaporator unit for evaporation of the solvent in step 234. The rate on the dosing pump to the evaporator unit is set so that the rate is not too high, which would cause incomplete solvent recovery, or too low, which would be inefficient. Dosing rates will vary depending on the solvent being evaporated. The recovered solvent is gathered in a collection vessel and pumped back to the extraction vessel to be reused in a subsequent extraction. Use of a solvent recovery system allows for reduced consumable costs.

After evaporation of the solution, the extracted resin is obtained in step 236, and it may be considered to be a purified resin as it has undergone one or more filtering processes. The spent plant material, along with the immiscible liquid, are removed through the bottom of the extraction vessel.

Figure 8:
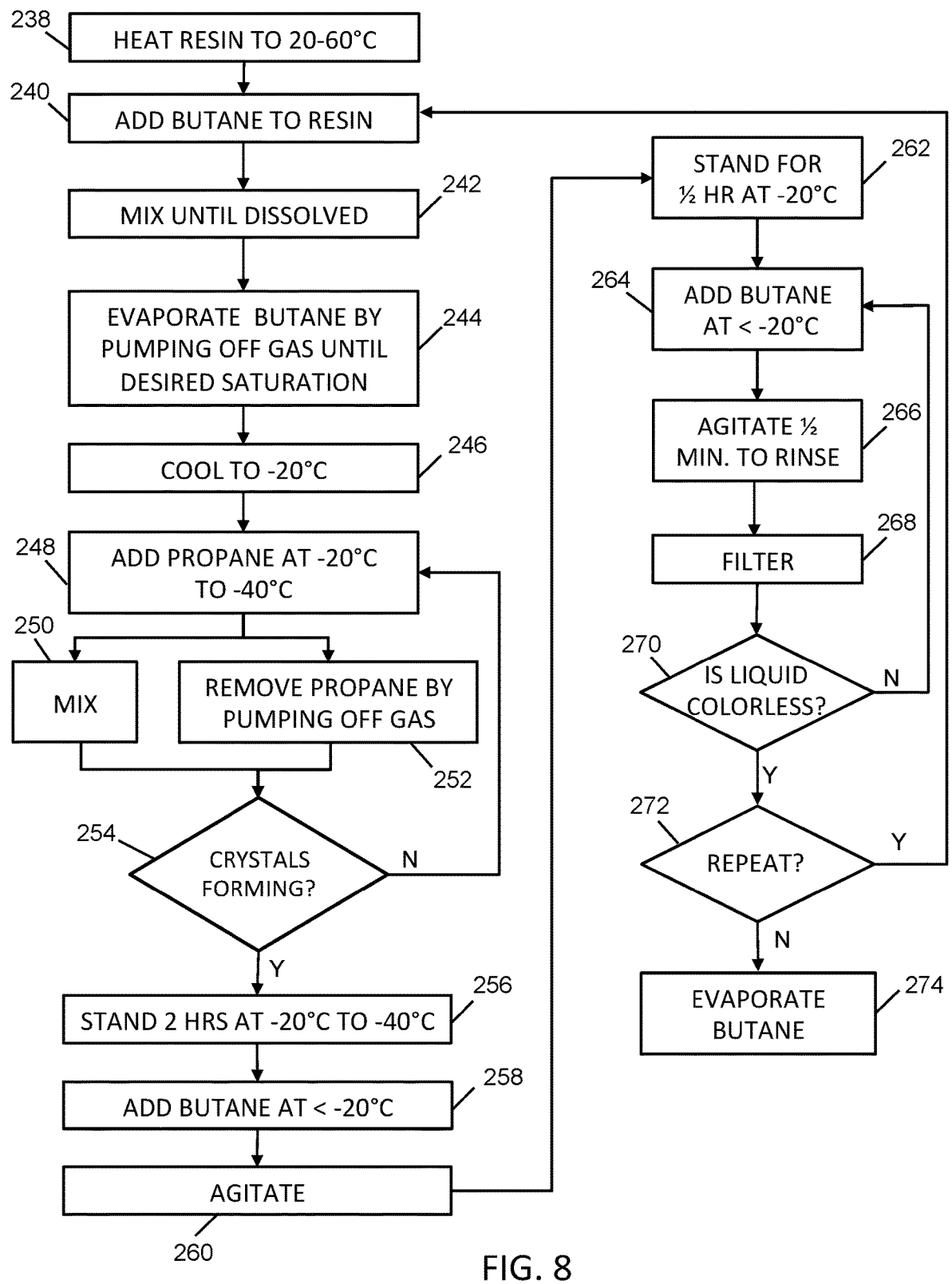
FIG. 8 is a detailed flowchart of the steps of the crystallization method, according to an embodiment of the present invention.

Referring to FIG. 8, a detailed method is shown for the crystallization of a desired compound present in an extracted plant resin. As described above, a suitable vessel for the crystallization is a pressure vessel with an agitation implement to allow for proper mixing of the resin and the solvents with which it will be mixed for the crystallization process.

The method starts with an extracted resin, which contains desirable compounds, being placed into crystallization vessel 161 and heated, in step 238, to 20° C.-60° C. The extracted resin is heated to the temperature necessary to ensure that its viscosity is suitable for mixing. In step 240, a volatile non-polar solvent is added to the resin. In this example, the volatile non-polar solvent is butane, which is injected into the bottom of the crystallization vessel 161 as a liquid at a pressure of about 140 kPa (20 psi). The butane to resin ratio is about 10:1 volume to volume, however, other ratios are possible provided that an excess of solvent is present.

In step 242, the contents of the crystallization vessel are mixed with the agitator 173 until the resin is substantially or fully dissolved in the butane. This is done by heating the vessel and/or the butane as it enters the vessel, and mixing the resin with the butane using an agitator. This is normally done at an elevated pressure. In the case where butane is used, these pressures can rise to above 0.7 MPa (100 psi) during normal operating procedures, although below 0.5 MPa (70 psi) is more typical. Using propane, pressures can reach 0.7 MPa (100 psi) during normal operation. In order to control the pressure in the crystallization vessel, it can be offgassed into a chilled condenser so that the butane vapor condenses back into a liquid. The dissolving process typically takes 10 minutes to multiple hours depending on the compounds being mixed and type of solvent used.

After dissolving the resin into the butane, the butane-resin solution is then supersaturated by removing butane from the solution by evaporation, in step 244. The removal of butane gas may be performed by heating the crystallization vessel 161, for example using water at a temperature of 20-40° C. in a jacket around the crystallization vessel. Heating may be used to prevent the evaporating butane from cooling the solution too much. If the butane-resin solution cools too much and the boiling stops, little or no further butane leaves the crystallization vessel 161. The butane-resin solution during this stage is typically maintained between 0° C., zero applied pressure and 20° C., 140 kPa (20 psi), but this is dependent on the rate at which the gaseous butane is removed and the rate at which heating is supplied to the solution. The gas pressure resulting from the evaporation dissipates into a condensing device 165, which may be a cold shell and tube exchanger that condenses the gas and directs it into a holding vessel, such as butane storage tank 162. In many cases this process is facilitated by the use of the pump 170, which is a piston pump, or a solvent recovery pump that is capable of creating a lower than atmospheric pressure in the crystallization vessel and which draws the butane out of the top of the crystallization vessel and into the condensing device.

The desirable level of supersaturation is the maximum saturation that the butane-resin solution can reach while still being of low enough viscosity to be mixed after the mixture has been cooled to a temperature of −40° C., at atmospheric pressure.

The final concentration of the butane-resin solution may be more accurately determined indirectly, by measuring its viscosity. For example, a viscosity of 1 mPa·s (cP) is a suitable viscosity of the solution, which allows the solution to be further cooled and still remain fluid enough to be mixed. For example, the butane-resin solution may have a viscosity of 1 mPa·s (cP) or below when the solution is at a temperature of 0° C., so that upon cooling the solution to −40° C., the solution's viscosity increases to only approximately 10,000 mPa·s (cP). Typically the ratio of butane to resin is between 1:1 and 3:1 after this first stage of evaporation. As the concentration of the desirable compound (THCA or CBDA or CBD) in the resin is normally not known, viscosity is the best metric to be used. The viscosity may, for example, be measured in an empirical fashion, in which a skilled operator watches the effects of the agitator on the solution as it is being mixed, and is able to estimate the viscosity based on the type of turbulence occurring at the surface of the solution. An estimate of the viscosity that is good to a factor of 50% is acceptable. In an industrial process a rotational viscometer may be used to determine the viscosity of the butane-resin solution in conjunction with the temperature of the solution. However, current viscometer technology for cryogenic fluids is limited due to the risk of explosion, and so the empirical method may be safer.

Once the butane-resin solution is adequately supersaturated, as determined by its viscosity rising to 1 mPa·s (cP), the crystallization vessel is optionally cooled to −20° C. in step 246, via a cooling jacket mounted around it. Chilling is not a necessary step but assists in preventing back pressure building up too quickly in the crystallization vessel and adds stability to the operation.

The evaporation of the butane decreases the temperature in the crystallization vessel and decreases the solubility of the resin, which may trigger instances of crystal precipitation.

Once cooled, a chilled, second volatile non-polar solvent is then injected into the butane-resin solution in step 248. In this example, the second volatile non-polar solvent is propane, e.g. from propane storage tank 164. The propane is injected with a head pressure of typically 280-550 kPa (40-80 psi). The propane is pre-chilled, e.g. using a heat exchanger 166 or chilled coil before injecting it into the butane-resin solution. The propane is typically at room temperature in the propane storage tank 164, and is cooled to −20° C. to −40° C. by the heat exchanger 166. Due to the cooling of the propane, its pressure may be reduced to 0-140 kPa (0-20 psi). Propane is injected until the ratio of propane to butane-resin solution is approximately 2:1 propane to butane-resin solution, volume to volume.

The second volatile non-polar solvent is selected such that the compound that is to be crystalized is less soluble in it than in the first volatile non-polar solvent. The boiling point of the second volatile non-polar solvent should be below that of the first volatile non-polar solvent. Also, the second volatile non-polar solvent should be miscible in the first volatile non-polar solvent. These requirements lead to a choice, for example, of butane for the first volatile non-polar solvent and propane for the second volatile non-polar solvent, when the extracted resin is a cannabis resin with THCA or CBDA or CBD.

The propane is thoroughly mixed into butane-resin solution in step 250 with the shear agitator 173. At the same time that the solution is being mixed, the mixture of solvents (mostly propane) is evaporated off in step 252. The pressure is reduced from whatever pressure has built up in the crystallization vessel, e.g. from 0-280 kPa (0-40 psi), to about −35 kPa (−5 psi) by evacuating the gaseous components of the solvents from the top of the crystallization vessel 161 into a secondary vessel such as a condenser 165, for example using a piston pump, a solvent recovery pump, a gas pump or similar, or a vacuum pump. The condensed solvent gases may then be separated and stored for further use.

In the crystallization vessel, the crystallization is promoted in three ways. Firstly, the second volatile non-polar solvent being introduced mixes with the first volatile non-polar solvent, decreasing the solubility of the desirable compound in the solution by adjusting the ratio of solvents towards a higher ratio of the second volatile non-polar solvent, which provides for a lower solubility of the desirable compound than the first volatile non-polar solvent. Secondly, the preferential evaporation of the second volatile non-polar solvent compared to the first volatile non-polar solvent decreases the temperature inside the crystallization vessel, which further decreases the solubility of the desired compound in the solution. Thirdly, the evaporation of both of the volatile non-polar solvents decreases the total amount of solvent in the mixture, and the temperature, which both increase saturation of the solution.

The crystals in this process grow to a uniform size so that rinsing is effective. The crystals are not so large that they entrain impurities, because the cooling occurs evenly throughout the solution, in contrast to other techniques in which cooling occurs from the outside of the vessel in.

The propane, and some of the remaining butane, are boiled off from the supersaturated solution under the reduced pressure at typically between 70 kPa and vacuum (10 and −14 psi), until crystals begin to form. If, in step 254, crystals are not formed, then more propane is injected as the process reverts to step 248. When crystals are seen forming, in step 254, agitation of the solution and crystals is stopped. Crystals typically start to form when the mixture is at a temperature of roughly −30° C. Propane injection in step 248, and evaporation in step 252, may be continued to maintain the temperature of the mixture low while the remaining crystals form, without the mixing step 250.

If, in step 254, the crystals have started to form, the crystallization vessel 161 is left to stand for 2 hours at a temperature of −20° C. to −40° C., in step 256. The time left to stand allows for the crystals to substantially or completely form.

Upon completion of the formation of crystals, the crystals may then be further purified by rinsing them with a chilled solvent, for example cold butane or propane, being careful to avoid redissolving the crystals by maintaining low temperatures at which the crystals are not soluble. By rinsing the crystals in a liquid in which they are insoluble allows any remaining impurities to be removed without affecting the desired product (i.e. crystals). To start the rinsing process, butane is injected, in step 258, through heat exchanger 166 such that it is colder than −20° C. Butane is added until there is a ratio of 4:1 of butane to the existing mixture. At this point the existing mixture includes crystals, propane, butane and the remainder of the resin, i.e. without the crystallized compound. The remainder of the resin includes numerous other non-crystallizing plant compounds. Alternately, the butane is added until liquid butane can be seen above the crystals.

In step 260, the resulting mixture is slowly and gently agitated in the crystallization vessel 161.

In step 262, the mixture is optionally allowed to stand for up to an hour (e.g. half an hour) while kept at −20° C. to −40° C. without agitation. In step 264, cold butane is again injected at a temperature that is between −20° C. and −40° C., with a pressure range of 70 to −70 kPa (10 to −10 psi). The butane is added so that the ratio is 3:1 butane to crystals, for example. In step 266, the mixture is gently agitated, for example for 0.5 minutes, to rinse the crystals.

In step 268, the liquid in the mixture, which is now a mixture of butane and non-crystallizing compounds, is removed out through the bottom of the crystallization vessel 161 and through filter 186. As a result, the crystals are collected in the filter 186.

In step 270 the removed liquid is checked to see whether it is colorless. If not, the process reverts to step 264 for further rinsing. If the liquid leaving is colorless, then this indicates that the crystals are fully rinsed and the process proceeds to step 272. In step 272 a decision is made as to whether the whole process should be repeated, to increase the purity of the crystals. If it is desired to increase the purity of the crystals, this is done by dissolving them and them recrystallizing the compound to remove entrainment. If the process is repeated, it reverts to step 238, in which the crystals are placed in the crystallization vessel 161 and then dissolved in step 242. If the process is not repeated, it ends with the residual butane on the crystals being evaporated in step 274. The crystals may then be distilled to be further purified.

D. Variations

The resin may be butane extracted cannabis resin, or a resin or oil extracted from another type of plant.

While the crystallization solvents (i.e. volatile non-polar solvents) have been described as being added sequentially, it is not expected or necessary that all of the first crystallization solvent is removed before the second crystallization solvent is added. When the second crystallization solvent is being removed, any remaining first crystallization solvent may also be removed at the same time.

While the system may be manually operated, by a single operator, other embodiments may be automated by replacing valves with pneumatically actuated valves and pressure transmitters.

In general, unless otherwise indicated, singular elements may be in the plural and vice versa with no loss of generality. For example, more than one desirable compound may be found in the resin, and they may all be crystallized together.

Numerical parameters in general are understood to be accurate to within 10%, or to the nearest significant figure, whichever provides for the greater range, unless otherwise specified.

Pressures are understood to be applied pressures above or relative to atmospheric pressure, except if the context indicates otherwise.

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. For example, various sensors, valves, jackets and pipes are not shown for clarity.

Accordingly, the specification and drawings are to be regarded in an illustrative, rather than a restrictive, sense.

It will be clear to one having skill in the art that further variations to the specific details disclosed herein can be made, resulting in other embodiments that are within the scope of the invention disclosed. All parameters, ratios, dimensions, materials, geometries and configurations described herein are examples only and may be changed depending on the specific embodiment. For example, the specific shapes of the various vessels may be different. Accordingly, the scope of the invention is to be construed in accordance with the substance defined by the following claims.

The invention claimed is:

1. A method for crystallizing a compound from a resin extracted from cannabis plants, wherein the compound is tetrahydrocannabinolic acid, cannabidiolic acid or cannabidiol, the method comprising:
mixing butane with the resin to form a solution;
evaporating butane from the solution to supersaturate the solution;
then, mixing propane with the solution, wherein the compound has a lower solubility in the propane than in the butane; and
removing the propane from the solution to cause a temperature of the solution to drop and the compound to form crystals.

2. The method of claim 1, wherein the butane is evaporated by pumping off the butane in its gaseous phase.

3. The method of claim 1, wherein the solution is maintained at a temperature of 0-20° C. and between a pressure of 0-140 kPa while evaporating the butane from the solution.

4. The method of claim 1, comprising cooling the solution to −20° C. after evaporating the butane from the solution.

5. The method of claim 1, wherein the propane is at a temperature of −20° C. to −40° C. when mixed with the solution.

6. The method of claim 1, comprising letting the crystals stand for 2 hours at −20° C. to −40° C.

7. The method of claim 1, comprising rinsing the crystals by, in order:
adding a third solvent to the crystals to form a mixture, wherein the crystals are insoluble in the third solvent;
agitating the mixture;
letting the mixture stand for up to 1 hour at −20° C.;
adding more third solvent at a temperature at or below −20° C. to the mixture;
agitating the mixture for half a minute; and
filtering the mixture to remove liquid from the mixture and obtain the crystals.

8. The method of claim 7 comprising, when the removed liquid is not colorless, repeating the rinsing.

9. The method of claim 7, comprising evaporating residual third solvent from the obtained crystals.

10. The method of claim 7, wherein the third solvent is butane.

11. The method of claim 7, wherein the third solvent is propane.

12. The method of claim 1, comprising obtaining the resin prior to crystallizing by:
mixing the cannabis plants with a fourth solvent in a vessel so that the resin in the cannabis plants dissolves in the fourth solvent;
introducing a liquid into a bottom of the vessel, wherein the liquid is immiscible with the fourth solvent and denser than the fourth solvent, so that the fourth solvent with dissolved resin floats on top of the liquid;
removing, through a screen that blocks the cannabis plants, the fourth solvent and dissolved resin from a top of the vessel; and
evaporating the fourth solvent to leave the resin.

13. The method of claim 12, wherein the liquid is water and the fourth solvent is butane.

14. The method of claim 12, wherein the liquid is water and the fourth solvent is propane, pentane, hexane, heptane or octane.

15. The method of claim 12, comprising filtering the removed fourth solvent and dissolved resin before evaporating the fourth solvent.

16. The method of claim 1, wherein the solution has a viscosity of 1±0.5 mPa·s at 0° C. after evaporating the butane.

* * * * *